United States Patent [19]

Brewer

[11] Patent Number: 4,920,126
[45] Date of Patent: Apr. 24, 1990

[54] BARBITURIC ACID DERIVATIVE AND TREATMENT OF LEUKEMIA AND TUMORS THEREWITH

[75] Inventor: Arthur D. Brewer, Puslinch, Canada

[73] Assignee: Uniroyal Chemical Ltd/Uniroyal Chemical Ltee, Don Mills, Canada

[21] Appl. No.: 192,459

[22] Filed: May 10, 1988

[51] Int. Cl.$^5$ .................. A61K 31/505; C07D 239/60
[52] U.S. Cl. .................... 514/274; 514/908; 544/301
[58] Field of Search ................ 544/301; 514/274, 908

[56] References Cited

U.S. PATENT DOCUMENTS

| | | | |
|---|---|---|---|
| 3,961,061 | 6/1976 | Kramer et al. | 544/301 |
| 4,229,454 | 10/1980 | Beriger | 544/301 |
| 4,283,444 | 8/1981 | de Sousa et al. | 544/301 |
| 4,329,460 | 5/1982 | Miyashita et al. | 544/301 |
| 4,349,552 | 9/1982 | Takaya et al. | 544/313 |
| 4,399,280 | 8/1983 | de Sousa et al. | 544/301 |
| 4,602,912 | 7/1986 | de Sousa et al. | 544/301 |
| 4,634,707 | 1/1987 | Brewer et al. | 544/301 |
| 4,636,508 | 1/1987 | Brewer et al. | 544/301 |
| 4,757,139 | 7/1988 | Kawaguchi et al. | 536/23 |
| 4,762,823 | 8/1988 | Watanabe et al. | 514/50 |

FOREIGN PATENT DOCUMENTS 614944 4/1974 Switzerland .
653840 1/1986 Switzerland .
2038631 7/1980 United Kingdom .

OTHER PUBLICATIONS

Takeda Chem. Ind. Ltd. Chem. Abst. vol. 60 (1964) 12026h, "Barbituric Acid Derivatives".
Becker et al, Chem. Abst. 99-48960g (1983), "Storage-Stable Moth-Proofing Formulation".

Primary Examiner—Cecilia Shen
Attorney, Agent, or Firm—John A. Shedden

[57] ABSTRACT

N-(2-Fluorophenyl)-1,2,3,4-tetrahydro-6-hydroxy-2,4-dioxo-5-pyrimidinecarboxamide, useful for regressing or inhibiting the growth of leukemia and tumors in mammals. The compound has the formula:

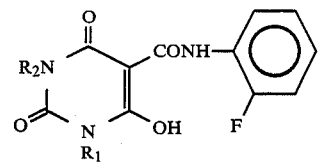

wherein $R_1$ and $R_2$ are selected from hydrogen or a cyclic or acyclic group which forms pyrimidine nucleosides or pseudo nucleosides, and the pharmacologically acceptable acid addition salts thereof.

3 Claims, No Drawings

BARBITURIC ACID DERIVATIVE AND TREATMENT OF LEUKEMIA AND TUMORS THEREWITH

TECHNICAL FIELD

This invention relates to a new barbituric acid derivative, viz., N-(2-fluorophenyl)-1,2,3,4-tetrahydro-6-hydroxy-2,4-dioxo-5-pyrimidine carboxamide, and to the pharmacologically acceptable addition salts thereof. More particularly, the invention relates to the indicated materials, which have been found to exhibit anti-leukemia and anti-tumor activity, to pharmaceutical compositions containing such materials as the therapeutically effective constituents thereof, and to a method utilizing the same for inducing the regression of leukemia and/or the inhibition of growth of tumors in mammals.

BACKGROUND ART

5-Pyrimidinecarboxamides, and particularly 5-carboxamides of barbituric acid, have previously been described as potential anti-cancer agents. Thus, Takeda Pharmaceutical Industries' Japanese Patent Publication No. 1,445/64, published on Feb. 14, 1964, suggests the use of compounds of the formula:

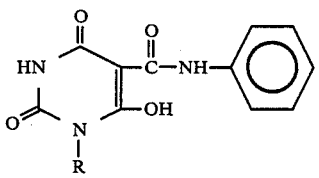

(I)

i.e., 5-phenylcarbamoylbarbituric acid (wherein R is hydrogen) and 1-substituted-phenylcarbamoylbarbituric acids (wherein R is alkyl or phenyl), for such purpose. When subjected to in vivo testing on Ehrlich Ascites carcinoma in mice the unsubstituted compound, but neither its 1-methyl nor 1-phenyl-substituted derivatives, exhibited anti-tumor activity. Chem & Pharm. Bull. (Tokyo) 8, 1021–1028 (1960).

Other 5-carboxamido-substituted barbituric acids such as:

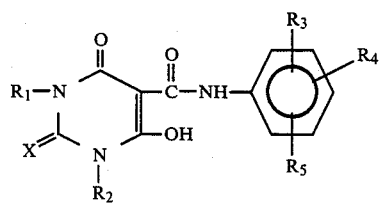

(II)

wherein X is oxygen or sulfur; $R_1$ and $R_2$ may each be alkyl, alkenyl, benzyl or unsubstituted or substituted phenyl; $R_3$ may be halogen, nitro or trihalomethyl; $R_4$ is hydrogen, halogen or trihalomethyl; and $R_5$ is hydrogen, halogen, methyl or methoxy, are also described in the patent literature. Such compounds are disclosed in Ciba-Geigy European Patent Publication No. 74,335 and in De Sousa et al., U.S. Pat. No. 4,283,444 granted on Aug. 11, 1981, as useful for protecting keratinous material, especially wool, from insect attack.

Analogs of similar barbituric acid derivatives have also been described in the literature. Thus, N-substituted-2-amidocarbonylthiobarbituric acids of the formula:

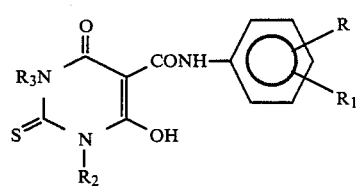

(III)

wherein $R^1$ is alkyl, alkenyl, various substituted alkyl, alkenyl or carbonyl, or optionally substituted aryl or aralkyl; $R^2$ and $R^3$ each independently is alkyl, alkenyl, cycloalkyl, aryl, aralkyl or hydrogen, provided that not more than one of $R^2$ and $R^3$ is hydrogen; and X is oxygen or sulfur, are disclosed in Bayer AG German Offen. No. 24 05 732 and in Kramer et al., U.S. Pat. No. 3,961,061 granted on June 1, 1976. These thiobarbituric acid derivatives are described as possessing insecticidal, acaricidal, fungicidal and bactericidal properties.

More recently, it has been disclosed in Brewer et al., U.S. Pat. No. 4,634,707, owned by the assignee of the present invention, the certain 5-carboxamido-2-thiobarbituric acid derivatives, viz., compounds of the formula:

(IV)

wherein R is hydrogen, 2 or 3-halo, 2-methyl, 4-fluoro, 4-($C_1$–$C_6$ alkoxyl), 2 or 4-trifluoromethyl, or hydroxyl, and $R_1$ is hydrogen; or R is 2-fluoro and $R_1$ is 4-fluoro; or R is 2-methoxy and $R_1$ is 5-methyl; and $R_2$ and $R_3$ are hydrogen atoms or carbohydrate residues; and the pharmacologically acceptable addition salts thereof, induce regression or inhibit the growth of leukemia and various malignant tumors in mammals.

It is among the objects of the present invention to provide a new 5-pyrimidinecarboxamide which is a useful anti-leukemia and anti-tumor agent, as well as pharmaceutical compositions, and therapeutic methods for utilizing the same.

Other objects and advantages of the invention will be apparent from the following detailed description of preferred embodiments thereof.

SUMMARY OF THE INVENTION

The novel 5-pyrimidinecarboxamide of this invention is N-(2-fluorophenyl)-1,2,3,4-tetrahydro-5-hydroxy-2,4-dioxo-5-pyrimidinecarboxamide, of the formula:

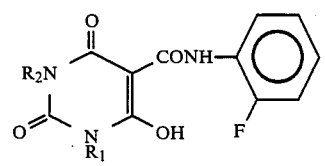

(V)

wherein each of $R_1$ and $R_2$ is selected from hydrogen or a carbohydrate residue.

As used herein, the term "carbohydrate residue" is intended to refer to those cyclic and acyclic groups which form pyrimidine nucleosides or pseudo nucleosides, e.g., materials including both cyclic and acyclic groups. Thus, when $R_1$ or $R_2$ is a carbohydrate residue, it may be furanosyl (e.g., arabinofuranosyl or ribofuranosyl), pyranosyl (e.g., glucopyranosyl), their deoxy derivatives, or their aliphatic analogs (e.g., hydroxyalkoxyalkyl or polyhydroxyalkyl groups) having from 2 to 12 carbon atoms in each of the alkoxy and alkyl moieties thereof, such as 2-hydroxyethoxymethyl or 2,3-dihydroxypropyl.

Addition salts of this compound may be formed with a variety of pharmacologically acceptable organic and inorganic salt-forming reagents. Addition salts may thus be formed by admixture of the 5-pyrimidinecarboxamide with one equivalent of a base, e.g., an organic amine such as triethylamine or N-methyl glucamine, and inorganic cations such as sodium, potassium or the like. The addition salts are, in general, crystalline solids which are relatively insoluble in both polar solvents such as water, methanol and ethanol and non-polar organic solvents such as diethyl ether, benzene, toluene and the like. They are somewhat soluble in aprotic solvents such as dimethylformamide and dimethylsulfoxide.

The 5-pyrimidinecarboxamide of the invention can exist in the form illustrated in Formula V or several other tautomeric forms. For ease of understanding, the compound of the invention will only be illustrated herein in the form shown in Formula V but will be understood to embrace the tautomers thereof, or a tautomeric mixture.

The novel 5-pyrimidinecarboxamide may be readily prepared by reacting barbituric acid with 2-fluorophenyl isocyanate, in the presence of a solvent or dispersing medium such as dimethylsulfoxide, pyridine, dimethylformamide, N-methylpyrrolidone, dimethylacetamide, sulfolane, tetrahydrothiophene oxide, acetonitrile, or a tertiary amine such as triethylamine. The molar proportions of the barbituric acid to the 2-fluorophenyl isocyanate may range from about 2:1 to 1:2, and are preferably from about 1.1:1 to 1:1.1, stoichiometric proportions generally sufficing. The reaction may be carried out at temperatures varying from about 0° to 200° C., usually at from about 24° to 160° C.; in most cases, the reaction proceeds quite well at temperatures of from about 80° to 100° C. Formation of the novel 5-pyrimidinecarboxamide is substantially complete within reaction periods varying about ½ to 6, and usually from about 2 to 4, hours.

Alternately, the compound may be prepared by other routes. For example, urea may be reacted with 2-fluorophenylaminocarbonylpropanedioic acid dialkyl ester (made by the action of 2-fluorophenyl-isocyanate on the malonic ester) to give N-(2-fluorophenyl)-1,2,3,4-tetrahydro-6-hydroxy-2,4-dioxo-5-pyrimidinecarboxamide. Alternatively, the 5-pyrimidinecarboxamide may be synthesized by oxidation, e.g., using hydrogen peroxide or a peracetic acid as the oxidizing agent, of the 2-thio analog:

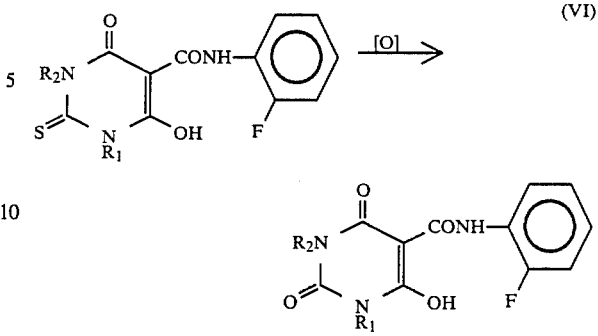

wherein $R_1$ and $R_2$ are as defined above. In yet another synthesis, a 2-amino analog of the 5-pyrimidinecarboxamide may be reacted with an alkali metal or alkaline earth metal compound, e.g., sodium hydroxide. (See e.g., British Published Application 2,152,047A, page 3, lines 22-25 for the analogous synthesis of 2-thio pyrimidinecarboxamides.) Other syntheses of analogous 2-thio or 2-alkylthio compounds may similarly be utilized.

The novel carboxamide is preferably prepared by suspending barbituric acid in dry pyridine with 2-fluorophenyl isocyanate. The suspension is gently warmed with stirring until the solids are dissolved, then boiled and filtered while hot. Upon cooling, solid N-(2-fluorophenyl)-1,2,3,4-tetrahydro-6-hydroxy-2,4-dioxo-5-pyrimidinecarboxamide precipitates. The solid is optionally washed with cold pyridine.

The novel compound of the invention is a cytotoxic agent useful to induce the regression of blood malignancies such as leukemia, as well as to inhibit the growth of solid and non-solid tumors. It may be used alone or in combination with other chemotherapeutic agents active for these purposes. As used herein, the terms "regression" and "inhibition" comprehend arresting or retarding the growth of the malignancy or other manifestation of the disease, as compared with the course of the disease in the absence of treatment.

Administration of the novel 5-pyrimidinecarboxamide to mice in amounts ranging from about 12 to 200 mg./kg., preferably from about 25 to 100 mg./kg., of body weight has been found effective to induce the regression of leukemia and to inhibit the growth of tumors. The interrelationship of dosages for mammals of other sizes and species is described by Freireich, E. J., et al., Quantitative Comparison of Toxicity of Anti-Cancer Agents in Mouse, Rat, Hamster, Dog, Monkey and Man, Cancer Chemotherapy, Reg. 50, No. 4,219-244, May 1966.

The dosage level may, of course, be adjusted to provide optimum therapeutic response. For example, several divided doses may be administered daily, or the dose may be proportionally reduced, as indicated by the exigencies of the therapeutic situation.

The active compound of the invention may suitably be administered parenterally, intraperitoneally, intravenously or orally. Solutions or dispersions of the active compound can be prepared in water, suitably mixed with a surfactant such as hydroxypropylcellulose. Dispersions can also be prepared by glycerol, liquid polyethylene glycols, and mixtures thereof, and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. For such uses the form nust be sterile and must be fluid to the extent necessary to provide easy syringability. It must be stable under the conditions of manufacture and storage and must be preserved against the contaminating action or microorganisms such as bacteria and fungi.

The carrier can be a solvent or dispersing medium containing, for example, water, ethanol, polyol (for example, glycerol, propylene glycol, and liquid polyethylene glycol, or the like), suitable mixtures thereof, and vegetable oils. The proper fluidity can be maintained, for example, by the use of a coating such as lecithin, by the maintenance of the required particle size in the case of a dispersion, and by the use of surfactants. Prevention of the action of microorganisms can be insured by various anti-bacterial and antifungal agents, for example, paraben, chlorobutanol, phenol, sorbic acid, thimerosal, or the like. In many cases it may be preferable to include isotonic agents, for example sugars or sodium chloride, in the dosage form. Prolonged absorption of the injectable formulations can be brought about by incorporating agents delaying absorption, for example, aluminum monostearate and gelatin, therein.

Sterile injectible solutions are prepared by incorporating the novel compound of the invention in the appropriate solvent, in admixture with various of the other ingredients enumerated above, as required, followed by filtered sterilization. Generally, dispersions are prepared by incorporating the sterilized active ingredient in a sterile vehicle which contains the dispersing medium and any other required ingredients. When, on the other hand, sterile powders are used to prepare sterile injectable solutions, it is preferred to subject a sterile, filtered solution of the desired ingredients to vacuum drying or freeze-drying, yielding a powder of the active ingredient plus any additional desired ingredients.

As used herein, "pharmaceutically acceptable, substantially nontoxic carrier or excipient" includes solvents, dispersing media, coatings, antibacterial and antifungal agents, isotonic and absorption delaying agents and the like. The use of such media and agents as carriers or excipients for pharmaceutically active substance is well known in the art. Except insofar as any conventional medium or agent is incompatible with the active ingredient or toxic, its use in the therapeutic formulations of the invention is contemplated. Supplementary active ingredients can also be incorporated in the therapeutic compositions.

It may be advantageous to formulate the compositions of the invention in unit dosage forms for ease of administration and uniformity of dosage. A unit dosage form, as used herein, refers to a physically discrete unit suitable for use as a unitary dosage for the mammalian subjects to be treated; each unit contains a predetermined quantity of active material calculated to produce the desired therapeutic effect, in association with the required pharmaceutically acceptable carrier. Specifications for unit dosage forms are dictated by and directly depend on (a) the unique characteristics of the active material and the particular therapeutic effect to be achieved, and (b) the limitations inherent in the art of compounding such an active material for the treatment of disease in living subjects having a diseased condition, without excessive cytotoxic side effects.

Regression of leukemia and inhibition of tumor growth may be attained, for example, by the use of daily dosing for up to 5 to 10 days, or longer. Multiple dosing, or dosing on any desired periodic basis, may also be utilized. The therapeutically active compound of the invention is thus administered in amounts sufficient to aid regression and inhibition of further growth of the leukemia or tumor, in the absence of excessive deleterious side effects of a cytotoxic nature.

Best Mode for Carrying Out the Invention

The invention will be described in greater detail in connection with the following specific examples illustrating the preparation and pharmacological testing of the 5-pyrimidinecarboxamide hereof:

Preparation of
N-(2-fluorophenyl)-1,2,3,4-tetrahydro-6-hydroxy-2,4-dioxo-5-pyrimidinecarboxamide A. Reaction of Barbituric Acid with 2-fluorophenyl isocyanate.

25 g of barbituric acid and 27 g of 2-fluorophenyl isocyanate were dissolved in 150 ml. of dry pyridine. The solution was heated with stirring to 80° C. for 4 hours. Upon cooling, a colored solid appeared. The solid and suspension were allowed to sit for about 12 hours. The solid was then collected and washed with cold pyridine.

YIELD: 43 gms [82.5%];

NMR (DMSO): a series of complex multiplets between 7.2 and 8.7$\delta$ (aromatic protons); a very broad peak centered on about 10.8$\delta$ and a broad peak at about 11.7$\delta$ (exchangeable protons attached to oxygen and nitrogen).

MELTING POINT: 295° to 300° C. (dec.)

MASS SPECTROMETRIC ANALYSIS: Major peaks at 265 (calc. 265); and at 155 and 111, being the pyrimidinecarbonyl fragment and (protonated) fluoroanilino fragments, respectively.

Comparison of Antitumor Activity In The Regression Of i.p.-Implanted Lymphoid Leukemia L1210

Samples of the test compound of the Example and a number of structurally-related control compounds were tested in accordance with National Cancer Institute test protocol 3LE31 (NCI Protocol 1.100, Cancer Chemotherapy Reports Part 3, Vol. 3, No. 2, September 1972) to determine the effects of the several compounds on i.p.-implemented L1210 leukemia (J. Nat'l. Cancer Inst. 13(5): 1328, 1953). Each test involved implantation of the leukemia cells in six DBA/2 mice, one sex per experiment, the male mice weighing a minimum of 18 grams and the female mice weighing a minimum of 17 grams, and all of the test animals being within a three gram weight range. The test compound was administered by i.p. injections, in 0.1 ml. doses of diluted ascitic fluid ($10^5$ cells per dose), commencing one day after the tumor implant and continuing daily for nine days.

The test animals were weighed and survivors recorded on a regular basis during a thirty day test period. The ratio of survival time for the treated and control animals (T/C) was determined as a percentage.

The tests were carried out at varying dosage levels and with varying numbers of repetitions, depending upon the results obtained with each test compound.

It has been statistically determined in the 3LE31 test system that an initial T/C value at least equal to 125% is necessary to demonstrate activity, while a reproducible T/C equal to or greater than 125% warrants further study. A reproducible T/C of 150% or higher is considered significant activity.

The number of mice "cured", viz., those surviving from each animal test group after the thirty day test period, is indicated in parenthesis following the T/C percentage data in the following table:

Comparative Activities Against i.p. Implanted L 1210 Leukemia Test Compounds

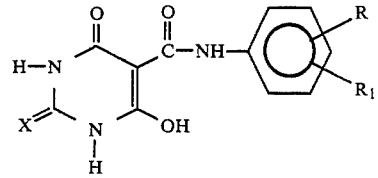

| Compound | R | $R_1$ | X | Dose (mg/kg) | T/C % | T/C % (repeat) | |
|---|---|---|---|---|---|---|---|
| Example 1 | 2-F | H | O | 200 | 226 | | |
| | | | | 100 | 148 | | |
| | | | | 50 | 128 | | |
| | | | | 25 | 121 | | |
| Control A | 2-F | 4-F | O | 200 | 108 | | |
| | | | | 100 | 106 | | |
| | | | | 50 | 111 | | |
| | | | | 25 | 109 | | |
| Control B (triethylamine salt) | 2-Cl | H | O | 200 | 108 | | |
| | | | | 100 | 102 | | |
| | | | | 50 | 111 | | |
| | | | | 25 | 102 | | |
| Control C | 3-Cl | 4-Cl | O | 200 | 103 | | |
| | | | | 100 | 102 | | |
| | | | | 50 | 94 | | |
| | | | | 25 | 100 | | |
| | | | | 12.5 | 98 | | |
| Control D [Control B, U.S. Pat. No. 4,634,707] | H | H | O | 200 | 137 | 134(2) | 166 |
| | | | | 100 | 149 | 179 | 142 |
| | | | | 50 | 124 | 134 | 112 |
| | | | | 25 | 118 | 115 | 108 |

| Compound | R | $R_1$ | X | Dose (mg/kg) | T/C % | T/C % (repeat) | T/C % (repeat) |
|---|---|---|---|---|---|---|---|
| Control E [Control D, U.S. Pat. No. 4,634,707] | 2-CH$_3$ | H | O | 200 | 124 | | |
| | | | | 100 | 106 | | |
| | | | | 50 | 104 | | |
| | | | | 25 | 108 | | |
| Control F [Control E, U.S. Pat. No. 4,634,707] | 4-OCH$_3$ | H | O | 200 | 117 | | |
| | | | | 100 | 105 | | |
| | | | | 50 | 105 | | |
| | | | | 25 | 109 | | |
| Control G [Control F, U.S. Pat. No. 4,634,707] | 4-OC$_2$H$_5$ | H | O | 200 | 115 | | |
| | | | | 100 | 115 | | |
| | | | | 50 | 110 | | |
| | | | | 25 | 110 | | |
| Control H (triethylamine salt) [Control C, U.S. Pat. No. 4,634,707] | H | H | O | 400 | | | 233 |
| | | | | 200 | 211 | | 179 |
| | | | | 100 | 143 | | 114 |
| | | | | 50 | 108 | | 112 |
| | | | | 25 | 108 | | 112 |
| Control I (triethanolamine salt) [Ex. 8, U.S. Pat. No. 4,634,707] | 2-F | H | S | 200 | 118 | | |
| | | | | 100 | 128 | | |
| | | | | 50 | 105 | | |
| | | | | 25 | 148 | | |
| Control J (triethylamine salt) | 2-F | H | S | 400 | None | | 184 |
| | | | | 200 | 155 | | 131 |
| | | | | 100 | 111 | | 119 |
| | | | | 50 | 118 | | None |
| | | | | 25 | 108 | | None |

| Compound | R | $R_1$ | X | Dose (mg/kg) | T/C % T/C % | T/C % (repeat) |
|---|---|---|---|---|---|---|
| Control K [Ex. 9, U.S. Pat. No. 4,634,707] | 2-F | 4-F | S | 200 | 133 | |
| | | | | 100 | 114 | |
| | | | | 50 | 113 | |
| | | | | 25 | 113 | |

-continued

Comparative Activities Against i.p.
Implanted L 1210 Leukemia Test Compounds

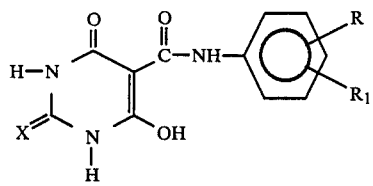

| Compound | R | $R_1$ | X | | | | | |
|---|---|---|---|---|---|---|---|---|
| Control L (triethylamine salt) | 2-F | 6-F | S | 200 | Toxic | | | |
| | | | | 100 | Toxic | | | |
| | | | | 50 | Toxic | | | |
| | | | | 25 | 103 | | | |
| Control M [Ex. 5, U.S. Pat. No. 4,634,707] | 3-F | H | S | 200 | Toxic | 155 | | |
| | | | | 100 | 128 | 117 | | |
| | | | | 50 | 114 | 113 | | |
| | | | | 25 | 114 | 106 | | |
| Control N | 4-F | H | S | 200 | Toxic | | | |
| | | | | 100 | 133 | | | |
| | | | | 50 | 112 | | | |
| | | | | 25 | 111 | | | |
| Control O [Ex. 2, U.S. Pat. No. 4,634,707] | 2-Cl | H | S | 400 | | Toxic | | |
| | | | | 200 | 206(1) | 152 | | |
| | | | | 100 | 127 | 130 | | |
| | | | | 50 | 118 | 123 | | |
| | | | | 25 | 106 | | | |
| Control P [Control A, U.S. Pat. No. 4,634,707] | 4-Cl | H | S | 200 | Toxic | Toxic | | |
| | | | | 100 | 125 | 120 111 | | |
| | | | | 50 | 121 | 109 102 | | |
| | | | | 25 | 110 | 103 103 | | |
| Control Q [Ex. 2, U.S. Pat. No. 4,634,707] | 2-CH$_3$ | H | S | 200 | Toxic | Toxic | | |
| | | | | 100 | 135 | 164 | | |
| | | | | 50 | 112 | 130 | | |
| | | | | 25 | 108 | 119 | | |

| Compound | R | $R_1$ | X | Dose (mg/kg) | T/C % | T/C % (repeat) | T/C % (repeat) | T/C % (repeat) | T/C % (repeat) |
|---|---|---|---|---|---|---|---|---|---|
| Control R [Ex. 1, U.S. Pat. No. 4,634,707] | H | H | S | 100 | 375(4) | 139(2) | 133 | 91(1) | 337(4) |
| | | | | 50 | 185 | 209 | 290 | 187 | 183 |
| | | | | 25 | 116 | 132 | 144 | 124 | 134 |
| | | | | 12.5 | 117 | 115 | 125 | | |
| | | | | 6.25 | 116 | | | | |
| | | | | 100 | | | 329(5) | 329(5) | 329(6) |
| | | | | 50 | | | 142 | 175 | 164 |
| | | | | 25 | | | 120 | 121 | 128 |
| | | | | 12.5 | | | 112 | | |

As may be seen from the preceding tabulation the compound of the present invention exhibited activity in the i.p.-implanted lymphoid leukemia test at dosage levels of 50 mg/kg or higher, and significant activity at a dosage of 200 mg/kg. Controls A–H are also barbituric acid derivatives. Controls A–C and E–G are substituted 5-pyrimidinecarboxamides and all failed to exhibit activity in the i.p.-implanted lymphoid leukemia test. In particular, the fluoro-substituted compound, Control A, and the chloro-substituted compounds, Controls B and C, exhibited no activity in the test. Thus, among the control barbituric acid derivatives, only the unsubstituted compounds, Controls D and H, exhibited activity.

Controls K–R are thiobarbituric acid derivatives. Controls I, K, M, O, Q and R are disclosed and claimed by Brewer et al. in U.S. Pat. No. 4,634,707, and all exhibited activity in the lymphoid leukemia tests.

From the preceding, it will be seen that, in accordance with the present invention, a novel compound, N-(2-fluorophenyl)-1,2,3,4-tetrahydro-6-hydroxy-2,4-dioxo-5-pyrimidinecarboxamide, is provided which exhibits substantial cytotoxic activity and induces regression and/or inhibits growth of leukemia and various malignant tumors in mammals.

It will be apparent that various changes may be made in the method of preparation and use of the compound of this invention. Accordingly, the preceding disclosure should be construed as illustrative only, and the scope of the invention should be interpreted in accordance with the claims appended hereto:

I claim:

1. A compound of the formula:

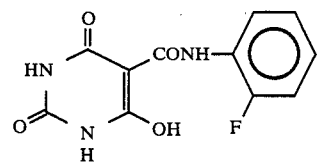

or the pharmacologically acceptable addition salts thereof.

2. A pharmaceutical composition for inducing regression or inhibiting the growth of lymphoid leukemia in mammals, comprising a therapeutically effective amount of the compound of claim 1 in admixture with a pharmaceutically acceptable, substantially nontoxic carrier or excipient.

3. A method for inducing regression or inhibiting the growth of lymphoid leukemia in mammals which comprises administering a therapeutically effective amount of the compound of claim 1 to mammals.

* * * * *